United States Patent
Sabba et al.

(10) Patent No.: US 11,953,630 B2
(45) Date of Patent: Apr. 9, 2024

(54) RADIATION DETECTOR

(71) Applicant: MURPHIL S.R.L., FERRARA (IT)

(72) Inventors: Nicola Sabba, Ferrara (IT); Elena Moretti, Santa Maria Maddalena Occhiobello (IT)

(73) Assignee: MURPHIL S.R.L., Ferrara (IT)

( * ) Notice: Subject to any disclaimer, the term of this patent is extended or adjusted under 35 U.S.C. 154(b) by 241 days.

(21) Appl. No.: 16/954,764

(22) PCT Filed: Dec. 19, 2018

(86) PCT No.: PCT/IB2018/060322
§ 371 (c)(1),
(2) Date: Jun. 17, 2020

(87) PCT Pub. No.: WO2019/123304
PCT Pub. Date: Jun. 27, 2019

(65) Prior Publication Data
US 2021/0088676 A1      Mar. 25, 2021

(30) Foreign Application Priority Data
Dec. 19, 2017   (IT) .......... 102017000146433

(51) Int. Cl.
*G01T 1/185*    (2006.01)
*A61K 51/00*    (2006.01)
*A61N 5/10*     (2006.01)

(52) U.S. Cl.
CPC ............. *G01T 1/185* (2013.01); *A61K 51/00* (2013.01); *A61N 5/1001* (2013.01); *A61N 2005/1021* (2013.01); *A61N 2005/1094* (2013.01)

(58) Field of Classification Search
CPC ...... G01T 1/185; A61K 51/00; A61N 5/1001; A61N 2005/1021; A61N 2005/1094
See application file for complete search history.

(56) References Cited

U.S. PATENT DOCUMENTS

| | | | |
|---|---|---|---|
| 4,483,816 A * | 11/1984 | Caldwell | G21G 1/12 976/DIG. 402 |
| 4,617,466 A * | 10/1986 | Menlove | G01T 3/00 376/257 |
| 5,095,217 A * | 3/1992 | Attix | H01J 47/024 250/374 |
| 8,729,488 B2 * | 5/2014 | Wilson | B07C 5/346 250/394 |
| 2002/0163987 A1 | 11/2002 | Ronaldson et al. | |

(Continued)

FOREIGN PATENT DOCUMENTS

| | | | | |
|---|---|---|---|---|
| FR | 1183892 | 7/1959 | | |
| FR | 2251911 A1 | 6/1975 | | |
| WO | WO-2008083313 A2 * | 7/2008 | ............. | A61B 5/055 |

OTHER PUBLICATIONS

Opinion on Patentability dated Nov. 9, 2022 in EP Application No. 18833116.9, 2 Pages.

*Primary Examiner* — Kiho Kim
(74) *Attorney, Agent, or Firm* — PEARNE & GORDON LLP; J. Gregory Chrisman

(57) ABSTRACT

A radiation detector, comprising two or more ionisation chambers (10), each of which comprises a main body (11), and which are arranged in such a way that the main bodies (11) delimit a measurement space (M) inside which a radiation source can be positioned.

15 Claims, 4 Drawing Sheets

(56) References Cited

U.S. PATENT DOCUMENTS

| | | |
|---|---|---|
| 2005/0094758 A1 | 5/2005 | Ronaldson et al. |
| 2006/0203951 A1 | 9/2006 | Ronaldson et al. |
| 2007/0235641 A1* | 10/2007 | Allberg ............... A61N 5/1075 |
| | | 250/252.1 |
| 2008/0242915 A1* | 10/2008 | Jackson ................ G21H 5/02 |
| | | 600/4 |
| 2013/0034198 A1 | 2/2013 | Chandrasekharan et al. |
| 2013/0154657 A1* | 6/2013 | Cooke ................. G01N 27/221 |
| | | 324/464 |

* cited by examiner

RADIATION DETECTOR

The present invention relates to a radiation detector. A preferred, but non-exclusive use of the detector according to the invention is in the field of nuclear medicine.

So-called "fractionation apparatus", that is, machines capable of fractionating a radioactive substance into different doses for patients, are among the machines most widely used in nuclear medicine. These machines, starting from a main "bulk" container which contains a sufficient amount of a radiopharmaceutical for various doses, are capable of drawing from the bulk container a pre-determined amount of a radiopharmaceutical, or dose. The dose is introduced into a syringe or a single-dose vial, ready for use.

For the purpose of the fractionation process, dose fractionation apparatus make use of radioactivity measuring devices commonly called "dose calibrators". These devices mainly consist of an ionisation chamber coupled with an electronic measuring instrument ("electrometer") and a control console with display of measurement data.

The task of such instruments/devices is to measure the activity contained in a syringe or in a vial with very high precision, which tends to be within ±2%.

In order to enable the necessary measuring precision, the ionisation chamber has a well-type conformation, i.e. it is in the form of a relatively deep cylindrical cavity in which the radioactive source to be measured is introduced from above.

The necessity of having a deep well is due to the following fundamental metrological needs.

First of all, the calibrator must enable a sufficient measuring efficiency. The well-type configuration makes it possible to surround the source with the detector, thus increasing the measuring efficiency. The loss of efficiency is in fact due to the solid angle (with the centre located in the radiation source) which subtends the hole for the introduction of the radioactive source.

Secondly, the calibrator must minimise, within acceptable limits (about 2-5%) the error in the relative positioning between the source and the detector. This error lies mainly in the fact that, in the typical practice of nuclear medicine, the radioactive sources are liquids contained in syringes or vials with variable volumes and shapes. The well-type configuration also enables this source of error to be reduced, in particular if the longitudinal dimension of the detector is much greater than the longitudinal dimension of the source to be measured.

Moreover, since the detectors are typically gas detectors, in order to ensure a low cost and considerable stability over time, it is necessary to pressurise the gas in order to increase the detection efficiency. The gas must be maintained under pressure (even approximately 15 bar) in the ionisation chamber and the ionisation chamber must have walls that are sufficiently "thin" to absorb as little radiation as possible (thus increasing the detection efficiency).

In order to be able to measure a liquid source in a syringe or vial with acceptable precision, it is therefore necessary to use a dose calibrator with an ionisation chamber with a well-type conformation. The fact of having well-type ionisation chambers implies an increase in the size of the instruments, as well as the necessity of accessing the instruments from above in order to introduce the radioactive source into the well, thus making it necessary to have additional overhead space for access.

Examples of known devices configured with geometries that could enable a reduction in the overall dimensions but are not suitable for measuring the small radioactive doses typical of nuclear medicine are described in documents US 2002/163987 and US 2013/034198.

The first document (US 2002/163987) relates to a technique for monitoring nuclear waste, in particular for monitoring the content of plutonium, and to a neutron detector. The device described comprises a plurality of neutron detectors which are independent from one another, so as to enable a specific analysis of the signals of each individual detector. In fact, the purpose of the device is to establish the content and distribution of neutron sources within the sample. For this to be possible, it is necessary for the individual detectors to be wholly independent from one another so as to enable a count of the pulses detected by each one of them and to determine, by means of mathematical models, the spatial distribution of the radioactive sources. In other words, the use of a certain number of independent detectors is a necessary condition for having spatial indications about the detection events, i.e. to be able to determine the spatial distribution of the radioactive sources. For this purpose, each detector has its own dedicated electronic amplification and discrimination system designed to measure pulses.

The device described in the second document (US 2013/034198) also comprises a series of detectors which are independent from one another and configured to detect fast neutrons. Each detector is provided with its own electronics for determining both the energy of the neutrons and the point of interaction inside the detector. In this case as well, the arrangement of the detectors and independence in management and measurement are necessary in order to determine the spatial distribution of the samples undergoing investigation.

The object of the present invention is to offer a radiation detector that enables the drawbacks of the currently available ionisation chambers to be overcome.

One advantage of the detector according to the present invention is that it requires considerably less overall space than the currently available chambers.

Another advantage of the detector according to the present invention is that it enables a considerable flexibility of positioning within the fractionation apparatus.

Additional features and advantages of the present invention will become more apparent from the following detailed description of one embodiment of the invention, illustrated by way of non-limiting example in the appended figures in which.

The radiation detector according to the present invention lends itself particularly well to use in a fractionation apparatus, configured for the preparation of pre-determined doses of a radiopharmaceutical.

The detector may be located inside a shielded booth together with other known accessories, including a support for a syringe, a support for a bulk container of the radiopharmaceutical, a feed circuit for feeding the radiopharmaceutical and saline solution or other substances, and electronics for controlling and managing the various devices.

The radiation detector according to the present invention comprises two or more ionisation chambers (10), each of which comprises a main body (11), intended to contain a measuring gas which, as is well known, ionises following exposure to radiation. A gas widely used to detect radiation is argon. The entity of ionisation that the gas undergoes, measurable by means of electronic circuits known in the art, depends on the intensity of the radiation it is exposed to. Ionisation chambers (10) are configured to detect alpha, beta or gamma sources.

Advantageously, the main bodies (11) are arranged in such a way as to delimit a measurement space (M) inside which a radiation source may be positioned. Essentially, instead of using a single ionisation chamber with a cylindrical shape, as is the case with current detectors, the present invention envisages the use of two or more ionisation chambers (10), arranged in such a way as to delimit a measurement space (M), whose shape and size can be selected based on the shape and size of the sources to be measured. Moreover, the ionisation chambers (10) can be mounted on movable supports so as to enable a change in the shape of the measurement space (M), or enable an opening of the measurement space (M) and facilitate the introduction of the source to be measured along a substantially horizontal direction of access. In other words, the source, i.e. the syringe containing the radiopharmaceutical, can be introduced into the measurement space (M) not from above, as is presently the case, but from the front, i.e. along a substantially horizontal direction of access. In general, and above all in the case of a fractionation apparatus, this enables a considerable reduction in the size of the booth intended to contain the detector. In fact, the booth can be dimensioned so as to contain the detector with modest margins heightwise, since the source to be detected has to be introduced into the measurement space (M) not from above, but horizontally.

A further advantage tied to the use of more than one ionisation chamber (10), rather than only one, is that each of them will have a relatively compact size, thus enabling them to withstand higher internal pressures with smaller wall thicknesses compared to the prior art. This results in a considerable increase in detection efficiency.

Figure 1:
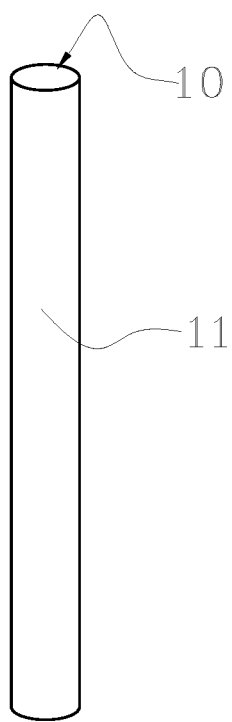
FIG. 1 shows an isometric view of an ionisation chamber according to the present invention.
Figure 2:
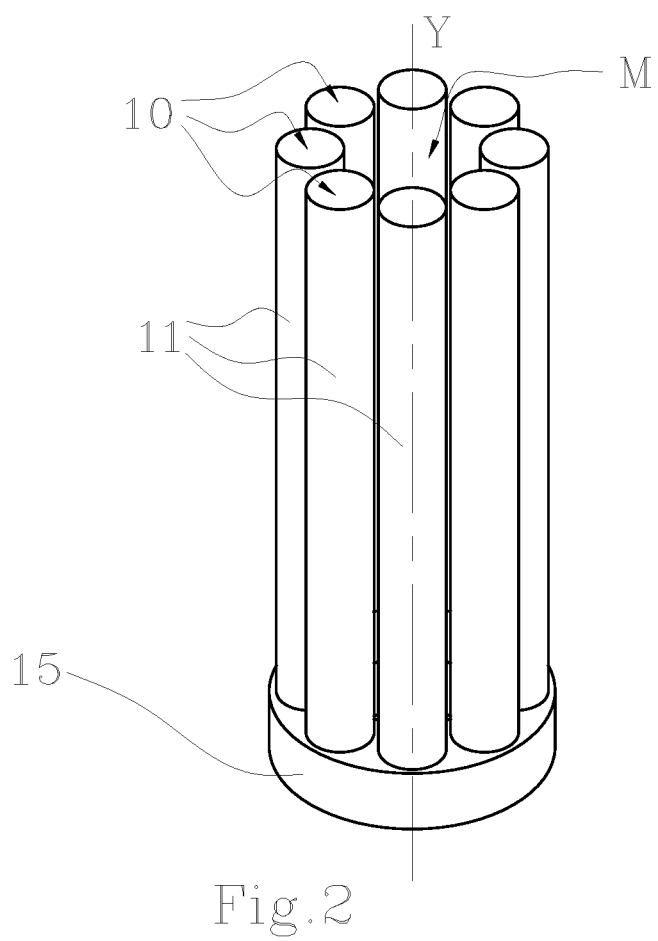
FIGS. 2 and 2a show, respectively, an isometric view and a top view of a first embodiment of a radiation detector according to the present invention.
Figure 2A:
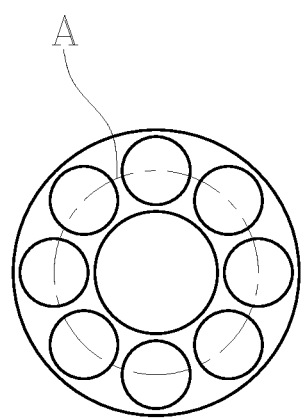

For example, the ionisation chambers (10) can be arranged so as to surround a measurement space (M) that is cylindrical or prismatic overall, endowed with a longitudinal axis (Y). The longitudinal axis (Y) is preferably vertically oriented. Examples of such an arrangement are shown in FIGS. 2, 4 and 5.

In a possible embodiment, the ionisation chambers (10) can be arranged in such a way that the main bodies (11) are distributed along a closed curve (C) lying in a plane which is perpendicular to the longitudinal axis (Y). In other words, the ionisation chambers (10) can be arranged in such a way as to surround a cylindrical space with a circular, oval or polygonal cross section, in relation to the shape of the source to be measured, and having a vertically oriented longitudinal axis (Y). In this case, the overall geometry of the measurement space (M) is of the well type, as in the current devices, but the use of more than one ionisation chamber (10) allows the shape of the measurement space (M) to be varied in a way that would be otherwise impossible using a single ionisation chamber.

Figure 3:
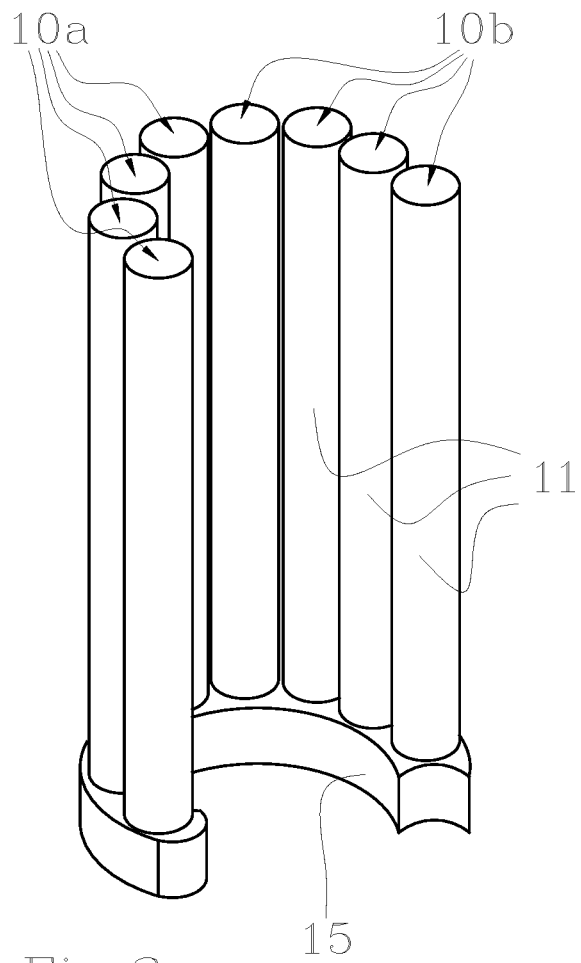
FIGS. 3 and 3a show, respectively, an isometric view and a top view of a second embodiment of a radiation detector according to the present invention, in an open configuration.
Figure 4:
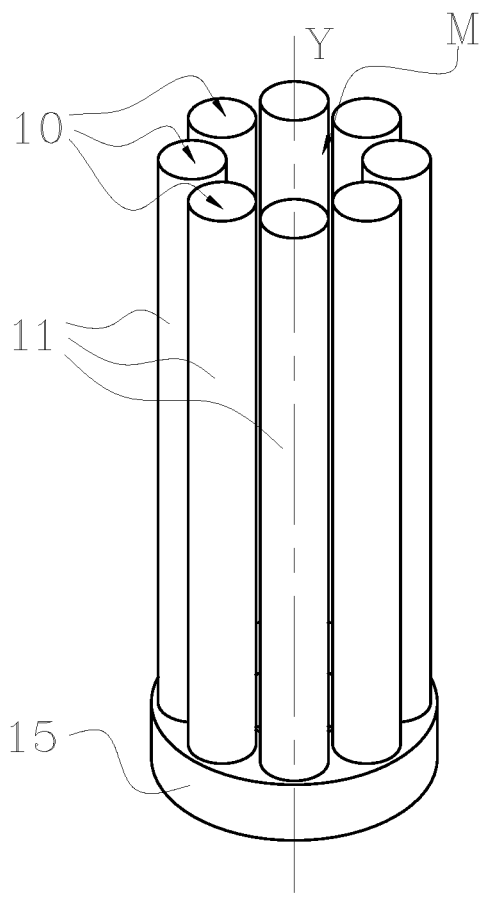
FIGS. 4 and 4a show, respectively, an isometric view and a top view of the detector in FIG. 3, in a closed configuration.
Figure 3A:
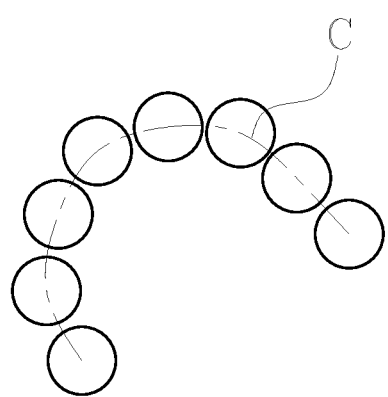
Figure 4A:
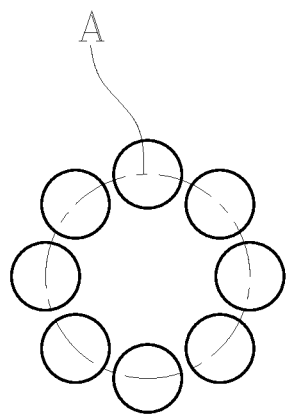
Figure 5:
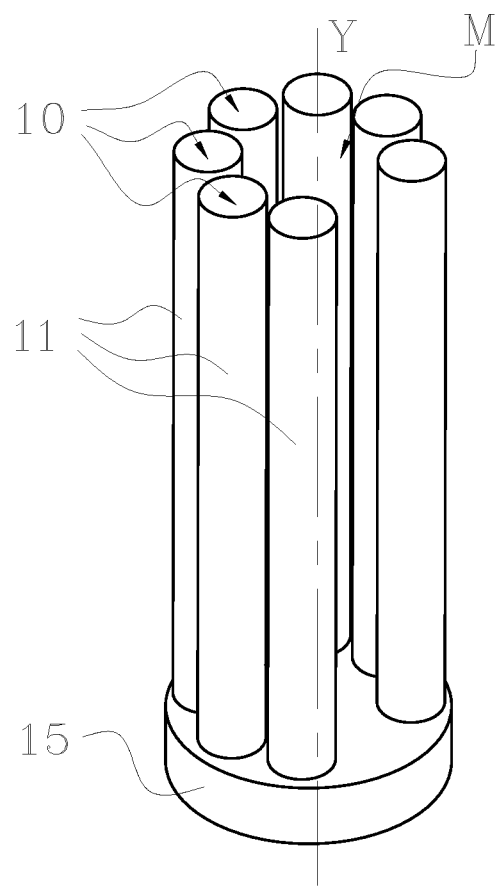
FIGS. 5 and 5a show, respectively, an isometric view and a top view of a third embodiment of a radiation detector according to the present invention.
Figure 5A:
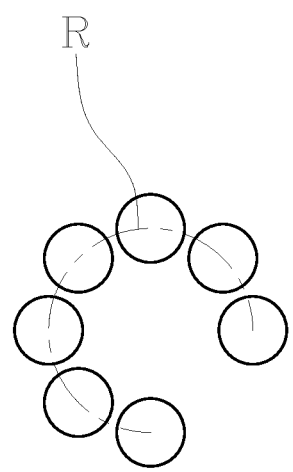

In a further embodiment, schematically illustrated in FIGS. 3 and 4, the detector according to the present invention comprises a plurality of ionisation chambers (10a,10b). A part of the ionisation chambers (10a) is movable relative to the remaining part of the ionisation chambers (10b) between a measurement position, in which the main bodies (11) are distributed along a closed curve (C), and a service position, in which the main bodies (11) are distributed along a line or an open curve (A). As previously noted, the closed curve (C) can be of any shape and the overall geometry of the measurement space (M) is cylindrical. Thanks to the use of more than one ionisation chamber (10a,10b), distributed as described, the measurement space (M) can be open so as to enable the introduction of the source along a horizontal direction, that is, not necessarily from above along the longitudinal direction of the measurement space (M), as is the case with current detectors. This means that the detector requires much less room for manoeuvre around it than is required by current detectors, which require the introduction of the source from above and thus all the space necessary for the introduction from above of the detector.

In a further possible embodiment, the ionisation chambers (10) can be arranged in such a way that the main bodies (11) are distributed along an open curve (R). In such a case the overall geometry of the measurement space (M) is again cylindrical, or well-type, but open at the side to facilitate the introduction of the source to be measured along a horizontal direction. The open curve (R) can be, for example, a circumferential arc which is concentric to the longitudinal axis (Y).

Figure 6:
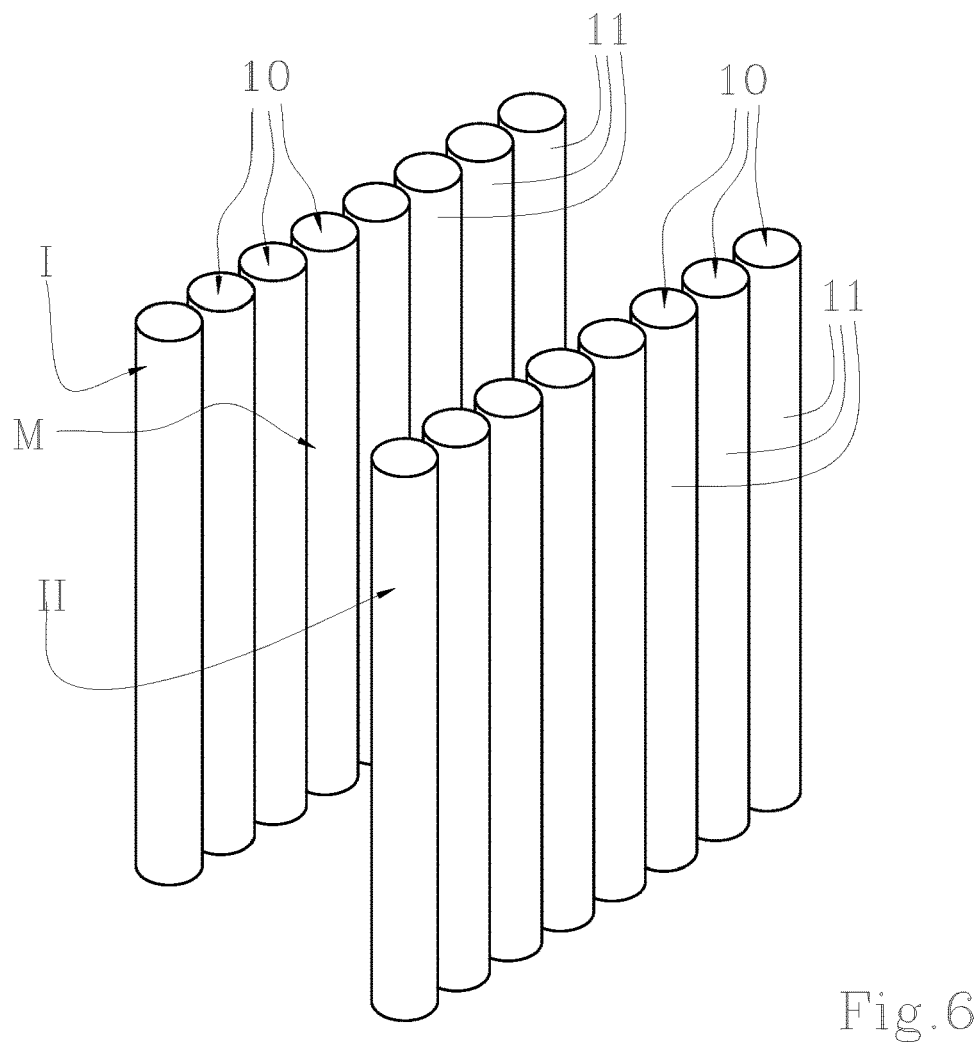
FIGS. 6 and 6a show, respectively, an isometric view and a top view of a fourth embodiment of a radiation detector according to the present invention.
Figure 6A:
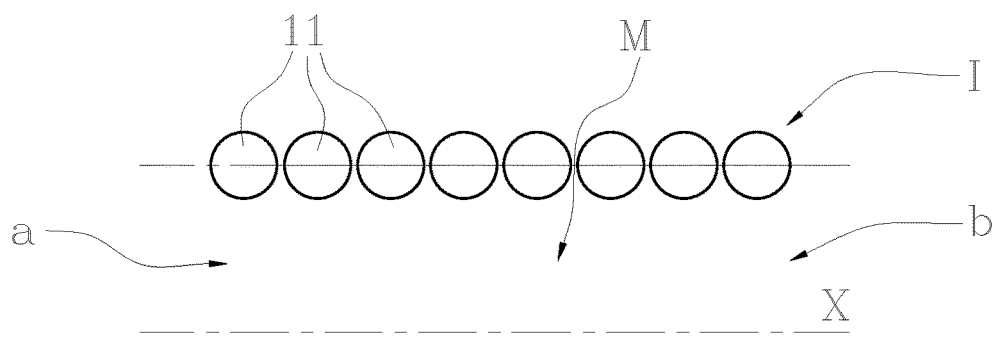
Figure 6A:
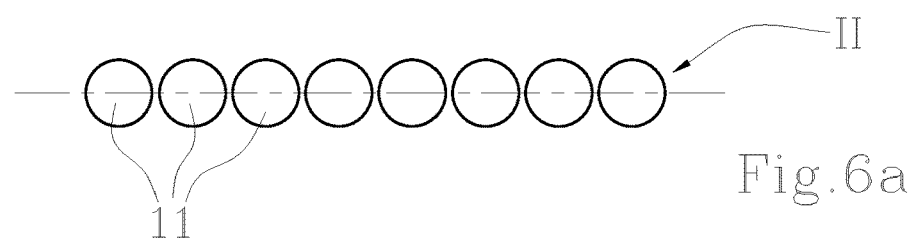

In a further possible embodiment, shown in FIGS. 6 and 6a, the ionisation chambers (10) can be arranged in such a way that the main bodies (11) are distributed along two rows (I, II) parallel to an alignment direction (X). In such a case, the measurement space (M) has a prismatic geometry, and can be open at both ends (a,b) of the two rows (I, II) of ionisation chambers (10), or else at one end only. The source to be measured can be introduced into the measurement space (M) along a direction which is parallel to the alignment direction (X) of the ionisation chambers (10). If the measurement space (M) is open at both ends, the source can be introduced and extracted rectilinearly along the alignment direction (X) in one way only, that is, the source can be introduced through a first end of the measurement space (M) and be extracted from the opposite end. If the measurement space (M) is closed at one end, introduction and extraction must obviously take place through the open end.

In a preferred, but non-exclusive embodiment, the main bodies (11) have a cylindrical conformation. This conformation offers high resistance to internal pressure, so the gas can be contained at high pressures, even 15 bar, without requiring large wall thicknesses, thus considerably improving detection efficiency. Furthermore, the longitudinal dimension, i.e. the length of the main bodies (11), can be considerably increased, enabling a further increase in detection efficiency.

The ionisation chambers (10) can be arranged with the main cylindrical bodies (11) oriented vertically, i.e. parallel to the longitudinal axis (Y) of the measurement space (M). The closed curve (C), open curve (A) and parallel rows (I, II) described previously are to be understood as lying in a plane which is perpendicular to the longitudinal axis (Y) of the measurement space (M).

In a possible embodiment, the main bodies (11) are independent from each other, i.e. each main body (11) is closed and delimits a containment volume for the gas used to detect radiation.

In an alternative embodiment, the main bodies (11) are connected to a manifold (15). In other words, the main bodies (11) and the manifold (15) delimit a closed volume for containing the measuring gas. The manifold (15) comprises a conduit for containing the measuring gas. For example, the manifold (15) can be ring-shaped, and the main bodies (11) can be connected to the manifold (15) projecting parallel to each other. The manifold (15) could also have a rectilinear shape or any other shape.

An electronic circuit, known in the art and thus not described in detail, can be connected to the ionisation chambers (10) in order to detect the overall ionisation of the gas and translate the detected ionisation into a radiation measurement. The circuit is commonly called an "electrometer". It enables, with different circuitries, the ionisation current produced by the incident radiation in the gas to be efficiently collected.

The electronic circuit is configured to add together the contributions of all of the ionisation chambers (10) in order to obtain a measurement of the total radiation. In other words, the electronic circuit is configured to integrate the ionisation current that is produced in the different ionisation chambers (10) in order to obtain a single electric signal.

For this purpose, each ionisation chamber (10) comprises an anode and a cathode, maintained at a potential difference by the electrometer itself and generally comprised between 150 and 500 Volts. The ions produced in the gas by the radioactive particles collect at the anode or cathode depending on their charge, thus producing a current. The ionisation currents produced in the various ionisation chambers (10) are integrated together in order to obtain a single electrical signal. The current is amplified by a circuit present in the electrometer, so as to generate a signal which is proportional to the ionisation current. The signal is then processed in order to be sent to a control and management module of the instrument (with a user interface). Finally, a calibration procedure, through the use of radioactive sources with known activity, enables the amplified and processed signal to be converted into units of radioactivity.

The invention claimed is:

1. A radiation detector, characterised in that it comprises (A) a plurality of ionisation chambers (10) and (B) an electronic circuit, wherein each of the ionisation chambers (10) contains a measuring gas and comprises a main body (11), wherein the plurality of ionisation chambers (10) are arranged in such a way that the main bodies (11) (*a*) define a wall which surrounds a measurement space (M) or (b) form two parallel rows between which is the measurement space (M); wherein the measurement space (M) is configured and sized and sufficiently small that the measurement space (M) can effectively receive a single syringe or vial or other container configured and sized to receive a predetermined dose of a radiopharmaceutical liquid to be administered to a single human patient with the single syringe or vial or other container being located sufficiently close to the main bodies (11) forming the measurement space (M) that the level of radiation emitted by the predetermined dose can be effectively measured by the radiation detector; wherein the electronic circuit is configured to detect the total ionisation of the measuring gas contained in the plurality of ionisation chambers (10), said radiation detector being configured and effective for detecting and determining the level of radiation emitted by the predetermined dose of the radiopharmaceutical liquid.

2. The detector according to claim 1, wherein the electronic circuit is configured to integrate the ionisation currents that are produced in the plurality of ionisation chambers (10) in order to obtain a single electrical signal.

3. The detector according to claim 1, wherein the plurality of ionisation chambers (10) are arranged in such a way that the main bodies (11) are distributed along a closed curve (C).

4. The detector according to claim 3, wherein the main bodies (11) are arranged uniformly adjacent one another in such a way that they define a single curved line.

5. The detector according to claim 1, wherein a first portion of the ionisation chambers (10*a*) is movable relative to the remaining portion of the ionisation chambers (10*b*) between a measurement position, in which the main bodies (11) are distributed along a closed curve (C), and a service position, in which the main bodies (11) are distributed along a line or an open curve (A).

6. The detector according to claim 5, wherein, when the detector is in the service position, a syringe can be moved horizontally into the detector.

7. The detector according to claim 1, wherein the plurality of ionisation chambers (10) are arranged in such a way that the main bodies are distributed along two parallel rows (I, II).

8. The detector according to claim 1, wherein each main body (11) has a cylindrical conformation.

9. The detector according to claim 1, wherein each main body (11) is closed and delimits a containment volume for the measuring gas.

10. The detector according to claim 1, wherein the main bodies (11) are connected to a manifold (15); the main bodies (11) and the manifold (15) delimit a closed volume for the containment of the measuring gas.

11. A fractionation apparatus for preparing doses of radiopharmaceuticals, comprising: a support for a syringe or other container configured and effective to receive a predetermined dose of a radiopharmaceutical; a support for a bulk container of a radiopharmaceutical; an hydraulic circuit, configured to connect the bulk container of the radiopharmaceutical and a saline solution source to the syringe or other container; characterised in that the fractionation apparatus comprises the radiation detector according to claim 1, wherein the support for said syringe or other container is located inside the measurement space (M).

12. A machine for preparing doses of radiopharmaceuticals, comprising a containment booth, provided with radiation shields, located inside which there is the fractionation apparatus according to claim 10.

13. The detector according to claim 1, wherein each of the main bodies (11) is a closed elongated tube.

14. The detector according to claim 1, wherein the measuring gas is argon.

15. The detector according to claim 1, wherein said single syringe or vial or other container is a single syringe.

* * * * *